US011351027B2

(12) United States Patent
Anderson et al.

(10) Patent No.: US 11,351,027 B2
(45) Date of Patent: Jun. 7, 2022

(54) PROSTHETIC HEART VALVE DELIVERY SYSTEM WITH CONTROLLED EXPANSION

(71) Applicant: Medtronic Vascular, Inc., Santa Rosa, CA (US)

(72) Inventors: Marc Anderson, Galway (IE); Patrick Griffin, Galway (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 84 days.

(21) Appl. No.: 16/890,651

(22) Filed: Jun. 2, 2020

(65) Prior Publication Data

US 2020/0289264 A1 Sep. 17, 2020

Related U.S. Application Data

(62) Division of application No. 15/369,154, filed on Dec. 5, 2016, now Pat. No. 10,716,666.

(51) Int. Cl.
*A61F 2/24* (2006.01)
(52) U.S. Cl.
CPC .......... *A61F 2/2433* (2013.01); *A61F 2/2418* (2013.01); *A61F 2/2436* (2013.01);
(Continued)
(58) Field of Classification Search
CPC .... A61F 2/2436; A61F 2/2418; A61F 2/2433; A61F 2/2469; A61F 2/2439;
(Continued)

(56) References Cited

U.S. PATENT DOCUMENTS 6,761,733 B2 * 7/2004 Chobotov ............... A61F 2/954
623/1.12
7,435,257 B2 10/2008 Lashinski et al.
(Continued)

FOREIGN PATENT DOCUMENTS

| CN | 104602646 | 5/2015 |
| WO | WO 2015173609 A1 | 11/2015 |
| WO | WO 2017151566 A1 | 9/2017 |

OTHER PUBLICATIONS

PCT communication dated Mar. 8, 2018 in corresponding PCT Appln.No. PCT/US2017/063220.

*Primary Examiner* — Erich G Herbermann
(74) *Attorney, Agent, or Firm* — Dicke, Billig & Czaja, PLLC

(57) ABSTRACT

A system for repairing a defective heart valve. The system includes a delivery device, a balloon and a prosthetic heart valve. The delivery device includes an inner shaft assembly and a delivery sheath assembly. The delivery sheath assembly provides a capsule terminating at a distal end. The prosthesis includes a stent carrying a prosthetic valve. In a delivery state, the capsule maintains the prosthesis in a collapsed condition over the inner shaft assembly, and the balloon is in a deflated arrangement radially between the prosthetic heart valve and the capsule. In a deployment state, at least a portion of the balloon and at least a portion of the prosthetic heart valve are distal the capsule. Further, the balloon is inflated and surrounds an exterior of at least a portion of the prosthetic heart valve. The balloon controls self-expansion of the prosthetic heart valve.

18 Claims, 18 Drawing Sheets

(52) U.S. Cl.
CPC .......... *A61F 2210/0014* (2013.01); *A61F 2230/0069* (2013.01); *A61F 2230/0078* (2013.01); *A61F 2250/0069* (2013.01); *A61F 2250/0071* (2013.01)

(58) Field of Classification Search
CPC ...... A61F 2/2487; A61F 2/243; A61F 2/2427; A61F 2/962; A61F 2/966; A61F 2210/0014; A61F 2250/0071; A61F 2230/0069; A61F 2230/0078; A61F 2002/249; A61F 2002/9665; A61F 2250/0069
See application file for complete search history.

(56) References Cited

U.S. PATENT DOCUMENTS

| | | | |
|---|---|---|---|
| 8,974,524 B2 | 3/2015 | Yeung et al. | |
| 9,173,738 B2 | 11/2015 | Murray et al. | |
| 9,364,637 B2 | 6/2016 | Rothstein | |
| 9,522,063 B2 | 12/2016 | Shipley et al. | |
| 2003/0125797 A1* | 7/2003 | Chobotov | A61F 2/07 623/1.13 |
| 2006/0020327 A1* | 1/2006 | Lashinski | A61B 17/0644 623/1.25 |
| 2006/0030923 A1* | 2/2006 | Gunderson | A61F 2/966 623/1.11 |
| 2010/0174362 A1* | 7/2010 | Straubinger | A61F 2/2427 623/2.11 |
| 2011/0251682 A1* | 10/2011 | Murray, III | A61F 2/2436 623/2.11 |
| 2012/0330342 A1 | 12/2012 | Jones et al. | |
| 2014/0277425 A1 | 9/2014 | Dakin | |
| 2016/0120646 A1 | 5/2016 | Dwork et al. | |
| 2016/0220367 A1 | 8/2016 | Barrett | |
| 2016/0220370 A1 | 8/2016 | Savage et al. | |

* cited by examiner

PROSTHETIC HEART VALVE DELIVERY SYSTEM WITH CONTROLLED EXPANSION

CROSS-REFERENCE TO RELATED APPLICATIONS

This application is a division of U.S. patent application Ser. No. 15/369,154, filed Dec. 5, 2016, entitled "Prosthetic Heart Valve Delivery System with Controlled Expansion," the entire teachings of which are incorporated herein by reference.

BACKGROUND

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable prosthetic valve is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With one type of stented prosthetic heart valve design, the stent frame is formed to be self-expanding. The valved stent is crimped down to a desired size and held in that compressed state within a sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

The stent frame must oftentimes provide and maintain (e.g., elevated hoop strength and resistance to radially compressive forces) a relatively complex shape in order to achieve desired fixation with the corresponding native anatomy. When forcibly compressed within an outer sheath to a size or diameter appropriate for transluminal delivery, the self-expanding stent frame thus stores significant energy. Upon retraction of the outer sheath, this stored energy is released as the stent frame rapidly self-expands, applying a high radial force on to native anatomy. Rapid release or expansion may be undesirable, possibly causing trauma, reshaping, etc., of the native anatomy.

SUMMARY

The inventors of the present disclosure recognized that a need exists for transcatheter heart valve repair systems that overcome one or more of the above-mentioned problems.

Some aspects of the present disclosure are directed toward a system for repairing a defective heart valve of a patient. The system includes a delivery device, a balloon and a prosthetic heart valve. The delivery device includes an inner shaft assembly and a delivery sheath assembly. The delivery sheath assembly is slidably disposed over the inner shaft assembly, and provides a capsule terminating at a distal end. The prosthetic heart valve includes a self-deploying stent carrying a prosthetic valve. The system is configured to provide at least a delivery state and an initial deployment state. In the delivery state, the capsule maintains the prosthetic heart valve in a collapsed condition over the inner shaft assembly, and the balloon is in a deflated arrangement radially between the prosthetic heart valve and the capsule. In the initial deployment state, at least a portion of the balloon and at least a portion of the prosthetic heart valve are located distal the distal end. Further, the balloon is in an inflated arrangement and surrounds an exterior of at least a portion of the prosthetic heart valve otherwise exposed distal the capsule. With this construction, the balloon slows or provides control over self-expansion of the prosthetic heart valve. In some embodiments, the balloon has a ring or toroid shape. In some embodiments, the system is configured such that the balloon can be disconnected from a remainder of the delivery device following deployment of the prosthetic heart valve. In other embodiments, the capsule forms an inflation lumen fluidly connected to an inflation chamber of the balloon.

Other aspects of the present disclosure are directed toward a method for repairing a heart valve of a patient. The method includes manipulating a heart valve replacement system in a delivery state to deliver a prosthetic heart valve of the system to a target site. The system further includes an inner shaft assembly, a delivery sheath assembly providing a capsule terminating at a distal end, and a balloon. The delivery state includes the capsule maintaining the prosthetic heart valve in a collapsed condition over the inner shaft assembly, and the balloon in a deflated arrangement radially between the prosthetic heart valve and the capsule. At least a portion of the balloon is exposed distal the distal end of the capsule. The exposed portion of the balloon is inflated. At least a portion of the prosthetic heart valve is positioned distal the distal end of the capsule. In this regard, the inflated balloon is disposed between the portion of the prosthetic heart valve and anatomy of the target site. The prosthetic heart valve is then deployed from the inner shaft assembly to the target site. In some embodiments, the method further includes disconnected the balloon from a remainder of the delivery site such that upon final deployment of the prosthetic heart valve, the balloon remains in place between the prosthetic heart valve and anatomy of the target site. In other embodiments, the method further includes incrementally retracting the capsule and balloon in tandem relative to the prosthetic heart valve.

DETAILED DESCRIPTION

Figure 1A:
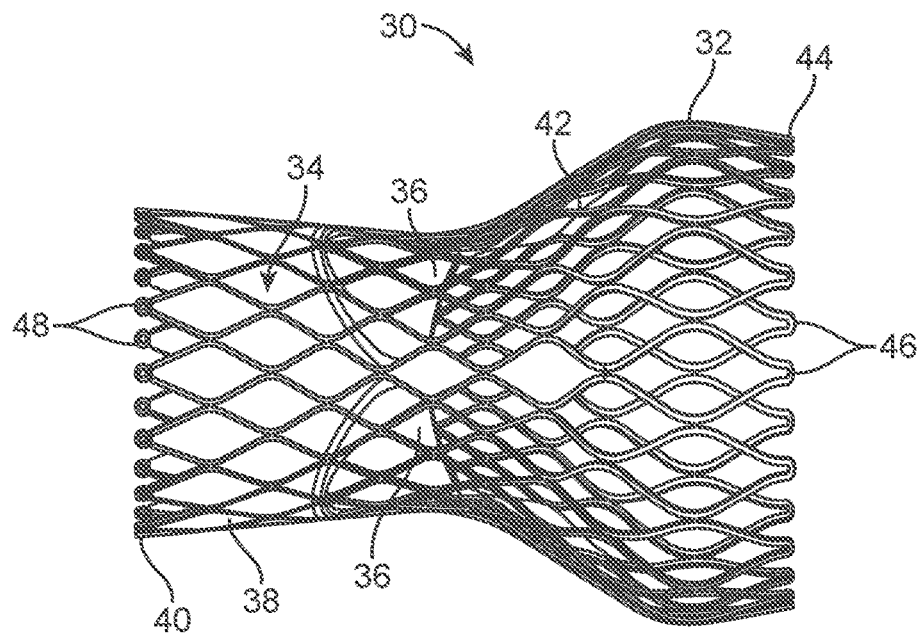
FIG. 1A is a side view of a stented prosthetic heart valve useful with systems, devices and methods of the present disclosure and in a normal, expanded condition.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

Aspects of the present disclosure provide a system for performing a therapeutic procedure on a defective heart valve of a patient, such as repairing a defective heart valve. The systems of the present disclosure generally include a prosthetic heart valve, a delivery device, and a balloon. The delivery device is configured to deliver the prosthetic heart valve through a patient's vasculature and deploy the prosthetic heart valve at a target site. The balloon assists in controlling deployment. In some embodiments, the balloon remains at the target site, and can optionally be considered a component of the prosthetic heart valve. In other embodiments, the balloon is removed from the target site following deployment of the prosthetic heart valve, and can optionally be considered a component of the delivery device. As a point of reference, "repairing" a defective heart valve is inclusive of the prosthetic heart valve implanted on to existing valve anatomy (e.g., the native valve leaflets are not removed, but are rendered non-functional by the implanted prosthetic heart valve), and is also inclusive of removing at least a portion of the native valve anatomy prior to implanting the prosthetic heart valve.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for repair (e.g., replacement) of a native aortic, mitral, pulmonic or tricuspid valve, or to repair (e.g., replace) a failed bioprosthesis, such as in the area of an aortic valve or mitral valve, for example.

In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1B:
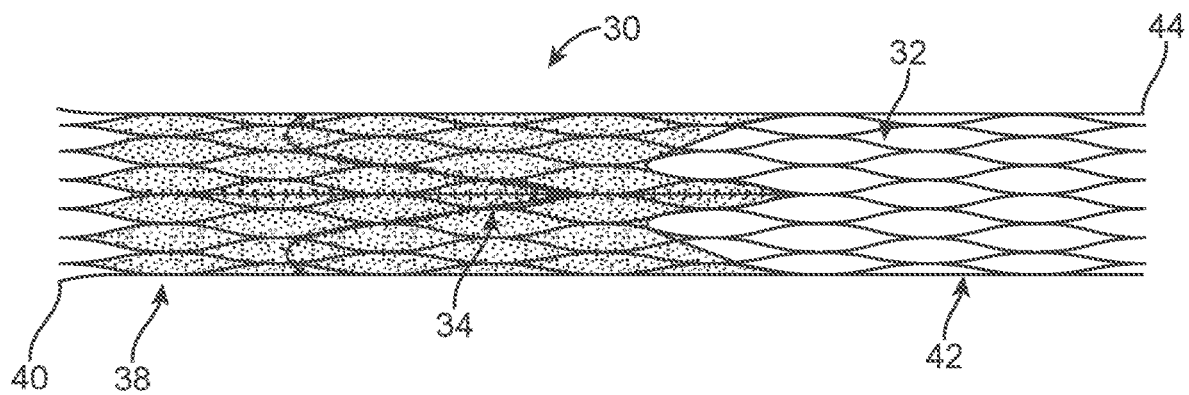
FIG. 1B is a side view of the prosthetic heart valve of FIG. 1A in a compressed condition.

With the above understanding in mind, one simplified, non-limiting example of a stented prosthetic heart valve 30 useful with systems, devices and methods of the present disclosure is illustrated in FIG. 1A. As a point of reference, the prosthetic heart valve 30 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 30 includes a stent or stent frame 32 and a valve structure 34. The stent frame 32 can assume any of the forms mentioned above, and is generally constructed so as to be self-expandable from the compressed condition (FIG. 1B) to the normal, expanded condition (FIG. 1A).

The valve structure 34 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 can be formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve. In some constructions, the valve structure 34 can comprise two or three leaflets that are fastened together at enlarged lateral end regions to form commissural joints, with the unattached edges forming coaptation edges of the valve structure 34. The leaflets 36 can be fastened to a skirt that in turn is attached to the frame 32. The upper ends of the commissure points can define an inflow portion 38 corresponding to a first or inflow end 40 of the prosthesis 30. The opposite end of the valve can define an outflow portion 42 corresponding to a second or outflow end 44 of the prosthesis 30. As shown, the stent frame 32 can have a lattice or cell-like structure, and optionally forms or provides crowns 46 and/or eyelets 48 (or other shapes) at the outflow and inflow ends 40, 44.

Figure 2:
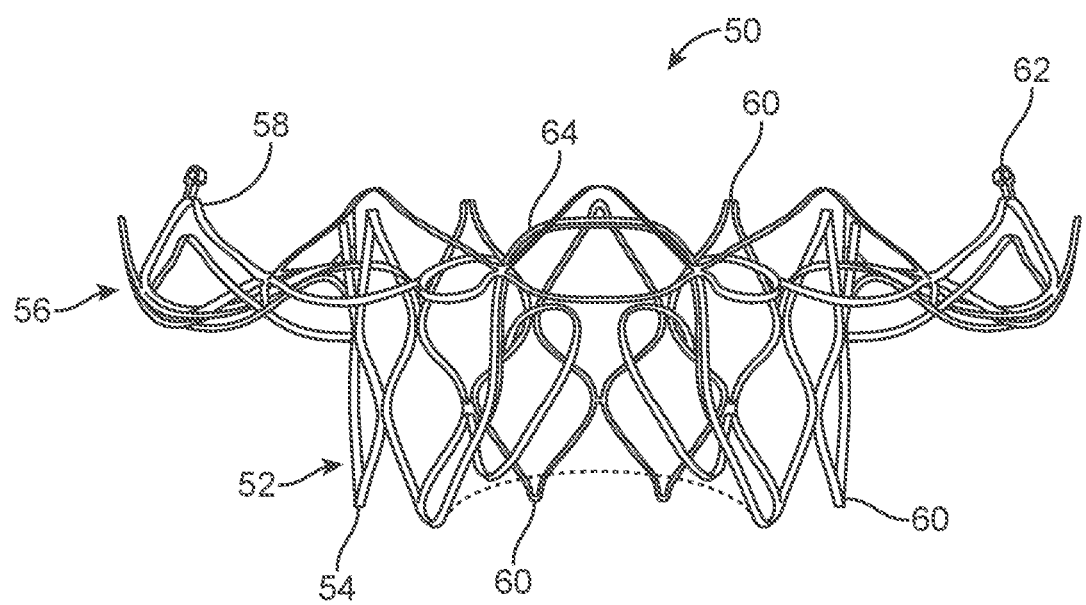
FIG. 2 is a side view of another exemplary prosthetic heart valve stent useful with systems, devices and methods of the present disclosure and in a normal, expanded condition.

With the one exemplary construction of FIGS. 1A and 1B, the prosthetic heart valve 30 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 2 illustrates another non-limiting example of a stent frame 50 portion of another prosthetic heart valve with which the systems, devices and methods of the present disclosure are useful. In the normal or expanded condition of FIG. 2, the stent frame 50 can be sized and shaped for mitral valve implantation. Though not shown, the valve structure attached to the stent frame 50 defines an outflow portion 52 arranged at a first or outflow end 54, and an inflow portion 56 arranged at a second or inflow end 58. As compared to the stent frame 32 of FIG. 1A, the inflow portion 56 can exhibit a more pronounced change in shape relative to the corresponding outflow portion 52. Regardless, the stent frame 50 can be forced and constrained to a compressed or collapsed condition (not shown, but akin to the shape of FIG. 1A) during delivery, and will self-expand to the natural or expanded condition of FIG. 2 upon removal of the constraining force(s). As reflected in FIG. 2, crowns 60 and/or eyelets 62 (or other shapes) optionally can be formed at one or both of the outflow and inflow ends 54, 58. Further, the stent frame 50 can optionally include or carry additional structural components, such as support arm(s) 64.

Figure 3:
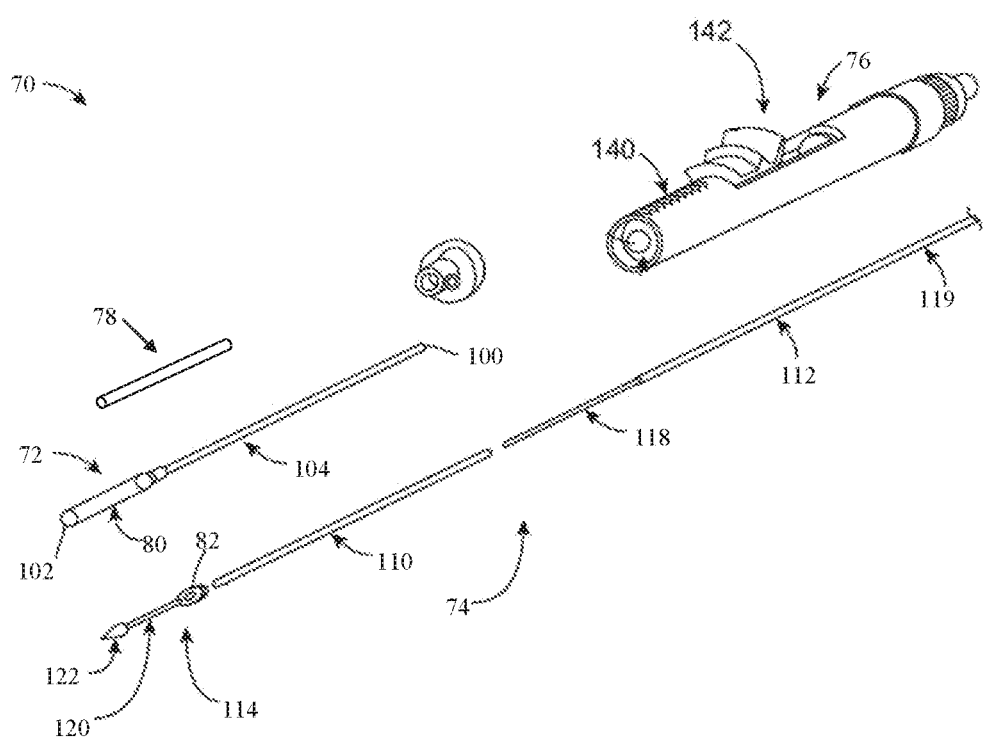
FIG. 3 is an exploded perspective view of a prosthetic heart valve delivery device in accordance with principles of the present disclosure.

With the above understanding of stented prosthetic heart valves in mind, one embodiment of a delivery device 70 for percutaneously delivering the prosthesis is shown in simplified form in FIG. 3. The delivery device 70 includes a delivery sheath assembly 72, an inner shaft assembly 74, and a handle assembly 76. A balloon 78 is also provided, and can optionally be viewed as a component of the delivery device 70 at various stages of use of the delivery device 70. Details on the various components are provided below. In general terms, however, the delivery device 70 and balloon 78 combine with a stented prosthetic heart valve (not shown) to form a system for performing a therapeutic procedure on a defective heart valve of a patient, such as repairing a defective heart valve. The delivery device 70 provides a loaded or delivery state in which a stented prosthetic heart valve is loaded over the inner shaft assembly 74 and is compressively retained within a capsule 80 of the delivery sheath assembly 72. For example, the inner shaft assembly 74 can include or provide a valve retainer 82 configured to selectively receive a corresponding feature (e.g., posts) provided with the prosthetic heart valve stent frame. The delivery sheath assembly 72 can be manipulated to withdraw the capsule 80 proximally from over the prosthetic heart valve via operation of the handle assembly 76, permitting the prosthesis to self-expand and partially release from the inner shaft assembly 74. When the capsule 80 is retracted proximally beyond the valve retainer 82, the stented prosthetic heart valve can completely release or deploy from the delivery device 70. The delivery device 70 can optionally include other components that assist or facilitate or control complete deployment. Regardless, the balloon 78 is disposed radially between the capsule 80 and the prosthetic heart valve in the delivery state. As described below, the balloon 78 is operable to control self-expansion or release of the prosthetic heart valve. In some embodiments, the balloon 78 is separable from a remainder of the delivery device 70, and can be left in place at a target native valve anatomy. In other embodiments, the balloon 78 is retracted from the patient with a remainder of the delivery device 70 following implantation of the prosthetic heart valve.

Various features of the components 72-76 reflected in FIG. 3 and as described below can be modified or replaced with differing structures and/or mechanisms. Thus, the present disclosure is in no way limited to the delivery sheath assembly 72, the inner shaft assembly 74, or the handle assembly 76 as shown and described below. Any construction that generally facilitates compressed loading of a stented prosthetic heart valve over an inner shaft via a retractable outer sheath or capsule is acceptable. Further, the delivery device 70 can optionally include additional components or features, such as a flush port assembly 90, a recapture sheath (not shown), etc.

In some embodiments, the delivery sheath assembly 72 defines proximal and distal ends 100, 102, and includes the capsule 80 and an outer shaft 104. The delivery sheath assembly 72 can be akin to a catheter, defining a lumen 106 (referenced generally) that extends from the distal end 102 through the capsule 80 and at least a portion of the outer shaft 104. The lumen 106 can be open at the proximal end 100 (e.g., the outer shaft 104 can be a tube). The capsule 80 extends distally from the outer shaft 104, and in some embodiments has a more stiffened construction (as compared to a stiffness of the outer shaft 104) that exhibits sufficient radial or circumferential rigidity to overtly resist the expected expansive forces of the stented prosthetic heart valve (not shown) when compressed within the capsule 80. For example, the outer shaft 104 can be a polymer tube embedded with a metal braiding, whereas the capsule 80 includes a laser-cut metal tube that is optionally embedded within a polymer covering. Alternatively, the capsule 80 and the outer shaft 104 can have a more uniform or even homogenous construction (e.g., a continuous polymer tube). Regardless, the capsule 80 is constructed to compressively retain the stented prosthetic heart valve at a predetermined diameter when loaded within the capsule 80, and the outer shaft 104 serves to connect the capsule 80 with the handle assembly 76. The outer shaft 104 (as well as the capsule 80) is constructed to be sufficiently flexible for passage through a patient's vasculature, yet exhibits sufficient longitudinal rigidity to effectuate desired axial movement of the capsule 80. In other words, proximal retraction of the outer shaft 104 is directly transferred to the capsule 80 and causes a corresponding proximal retraction of the capsule 80. In other embodiments, the outer shaft 104 is further configured to transmit a rotational force or movement onto the capsule 80.

The inner shaft assembly 74 can have various constructions appropriate for supporting a stented prosthetic heart valve within the capsule 80. The inner shaft assembly 74 can form or define at least one lumen (not shown) sized, for example, to slidably receive a guide wire (not shown). In some embodiments, the inner shaft assembly 74 includes an intermediate shaft or tube 110, a proximal shaft or tube 112 and a retention sub-assembly 114. The intermediate tube 110 is optionally formed of a flexible polymer material (e.g., PEEK), and is sized to be slidably received within the delivery sheath assembly 72. The proximal tube 112 can include, in some embodiments, a leading portion 118 and a trailing portion 119. The leading portion 118 serves as a transition between the intermediate and proximal tubes 110, 112, and in some embodiments is a flexible polymer tubing having a diameter slightly less than that of the intermediate tube 110. The trailing portion 119 can have a more rigid construction, configured for robust assembly with the handle assembly 76, such as a metal hypotube. Other constructions are also envisioned. For example, in other embodiments, the intermediate and proximal tubes 110, 112 are integrally formed as a single, homogenous tube or solid shaft.

The retention sub-assembly 114 includes the valve retainer 82, an inner support shaft 120 and a tip 122. The inner support shaft 120 is sized to be slidably received within the lumen 106 of the delivery sheath assembly 72, and is configured for mounting to the intermediate tube 112 (either directly or via the valve retainer 82). The inner support shaft 120 can be a flexible polymer tube embedded with a metal braid. Other constructions are also acceptable so long as the inner support shaft 120 exhibits sufficient structural integrity to support a loaded, compressed stented prosthetic heart valve (not shown). The tip 122 forms or defines a nose cone having a distally tapering outer surface adapted to promote atraumatic contact with bodily tissue. The tip 122 can be fixed or slidable relative to the inner support shaft 120.

The handle assembly 76 generally includes a housing 140 and one or more actuator mechanisms 142 (referenced generally). The housing 140 maintains the actuator mechanism(s) 142, with the handle assembly 76 configured to facilitate sliding movement of the delivery sheath assembly 72 relative to other components (e.g., the inner shaft assembly 74). The housing 140 can have any shape or size appropriate for convenient handling by a user.

Figure 4A:
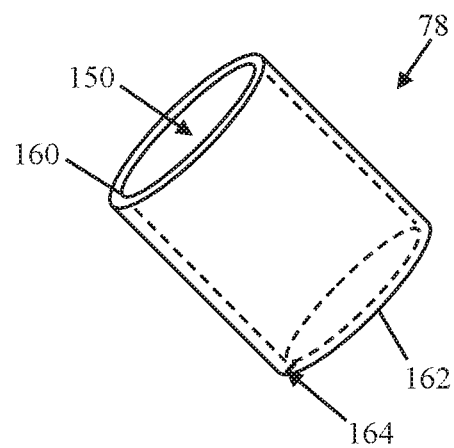
FIG. 4A is a perspective view of a balloon useful with the delivery device of FIG. 3.
Figure 4B:
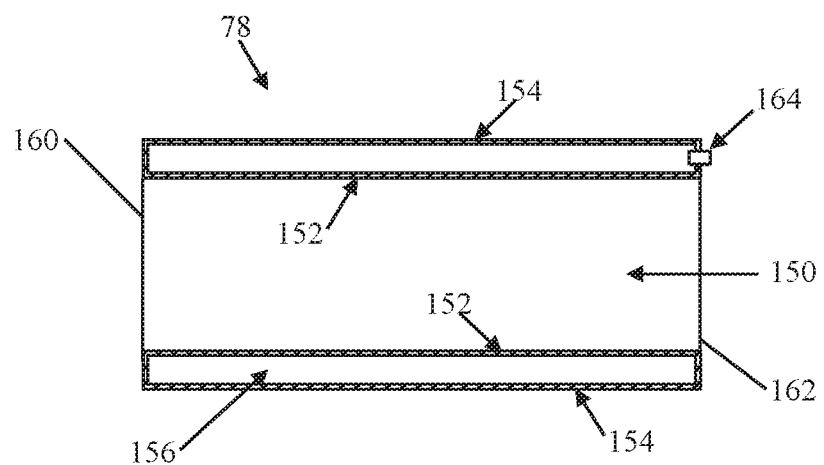
FIG. 4B is a longitudinal cross-sectional view of the balloon of FIG. 4A.

With the above general explanations of exemplary embodiments of the components 72-76 in mind, one embodiment of the balloon 78 is shown in FIGS. 4A and 4B. The balloon 78 is toroid-shaped or hollow, defining a central passage 150 generally sized and shaped for receiving a prosthetic heart valve (not shown). As best shown in FIG. 4B, a material of the balloon 78 can be wrapped on to itself to effectively provide inner and outer walls 152, 154 that generate the toroid shape. The central passage 150 is circumscribed by the inner wall 152. An inflation chamber 156 is defined between the walls 152, 154. The central passage 150 is open at opposing, first and second ends 160, 162 of the balloon 78. The inflation chamber 156 is closed at the end 160, 162 such that an inflation medium (not shown) forced into the inflation chamber 156 (e.g., via a port 164) causes the balloon 78 to expand. In some embodiments, the balloon 78 is configured (e.g., materials, shape set properties, etc.) such that expansion occurs primarily in the radial direction. The balloon 78 can be formed from any conventional, surgically safe material such as polyurethane, Nylon 12, polyethylene terephthalate, Pebax, materials conventionally used with angioplasty balloons, etc.

Figure 5A:
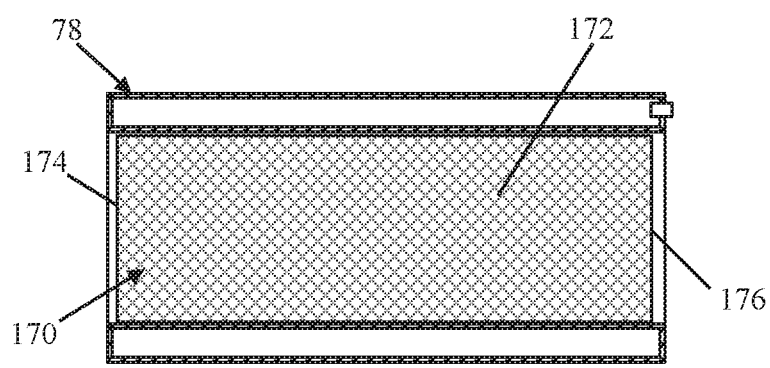
FIG. 5A is a simplified cross-sectional view of the balloon of FIG. 4A associated with a prosthetic heart valve.
Figure 5B:
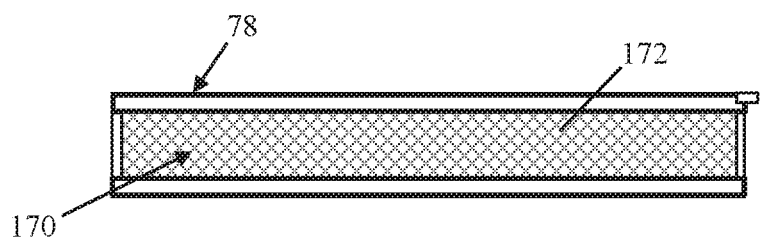
FIG. 5B is a simplified cross-sectional view of the arrangement of FIG. 5A with the prosthetic heart valve in a collapsed condition.
Figure 5C:
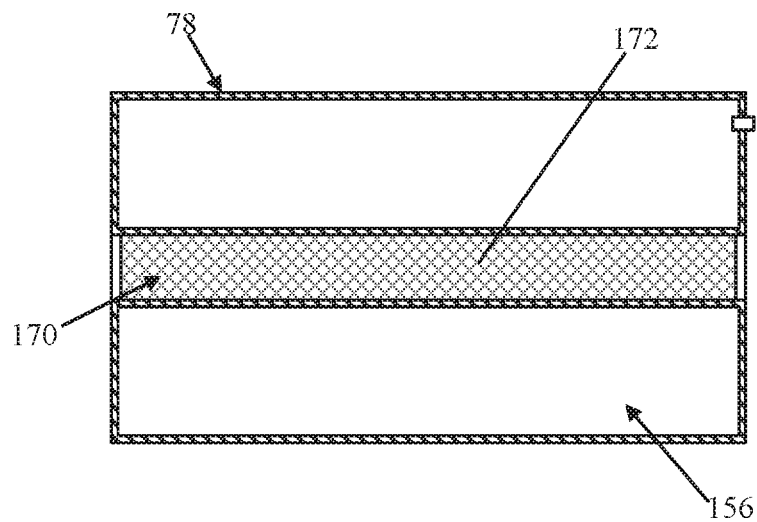
FIG. 5C is a simplified cross-sectional view of the arrangement of FIG. 5B with the balloon in an inflated arrangement.

In some embodiments, the balloon 78 is sized and shaped in accordance with a size and shape of the prosthetic heart valve in question. For example, FIG. 5A illustrates in the balloon 78 assembled over a prosthetic heart valve 170, with the prosthetic heart valve 170 in the normal or expanded condition. For ease of illustration, only the stent frame 172 of the prosthetic heart valve 170 is shown. Commensurate with the descriptions above, the prosthetic heart valve 170 is disposed within the central passage 150 of the balloon 78. In some embodiments, a length of the balloon 78 is greater than a length of the prosthetic heart valve 170 in the normal or expanded condition, with the balloon 78 extending beyond one or both of the inflow and outflow ends 174, 176 of the prosthetic heart valve 170. The balloon 78 can be attached to the prosthetic heart valve 170 in some embodiments (e.g., the balloon 78 can be bonded to an ePTFE skirt commonly provided with prosthetic heart valves); with these and other embodiments, the balloon 78 can be considered a component of the prosthetic heart valve 170. Regardless, resiliency and other properties of the balloon 78 are optionally selected such that the balloon 78 will stretch, fold or otherwise comply with a shape of the prosthetic heart valve 170 when forced to the compressed or crimped condition as in FIG. 5B. As shown, a length of the balloon 78 can be greater than a length of the prosthetic heart valve 170 in the compressed condition. Further, resiliency and other properties of the balloon 78 are such that the balloon 78 can be inflated (e.g., pressure or an inflation medium (e.g., gas or liquid) is generated in the inflation chamber 156), whereby the balloon 78 experiences radial expansion as in FIG. 5C.

Figure 6:
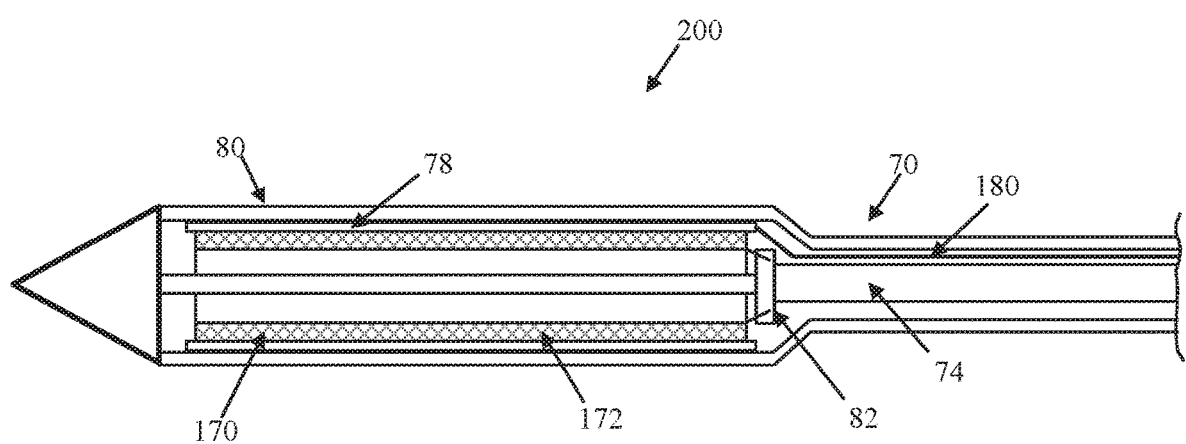
FIG. 6 is a simplified cross-sectional view of a portion of a system in accordance with principles of the present disclosure, including the delivery device of FIG. 3 and a prosthetic heart valve.

A simplified representation of a portion of a system 200 in accordance with principles of the present disclosure, and including the delivery device 70 and the prosthetic heart valve 170 (including the balloon 78 attached thereto) as described above, is provided in FIG. 6. In the delivery state of FIG. 6, the prosthetic heart valve 170 is loaded and maintained in a collapsed or crimped condition over the inner shaft assembly 74 by the capsule 80. The stent frame 172 is releasably connected to the valve retainer 82. The balloon 78 is in a deflated arrangement and is disposed over the prosthetic heart valve 170, radially between the stent frame 172 and the capsule 80. That is to say, the deflated balloon 78 is exteriorly located relative to the stent frame 172. The capsule 80 is longitudinally moveable or slidable relative to the balloon 78 and the prosthetic heart valve 170

(and vice-versa). A supply line 180 defining an inflation lumen (hidden) is fluidly connected to the inflation chamber 156 (hidden in FIG. 6, but shown, for example, in FIG. 4B) and extends proximally from the balloon 78 to the handle assembly 76 (FIG. 3) for connection to a pressurized inflation medium source (not shown) such as saline liquid, gas, etc. For example, the supply line 180 can be a tubular member attached to the port 164 (FIG. 4B) in a severable or detachable manner (e.g., friction fit). In some embodiments, the delivery device 70 can further include one or more mechanisms (e.g., a small guillotine-type device at a distal end of the supply line 180) that facilitate user-prompted severing of the supply line 180 from the balloon 78.

Figure 7A:
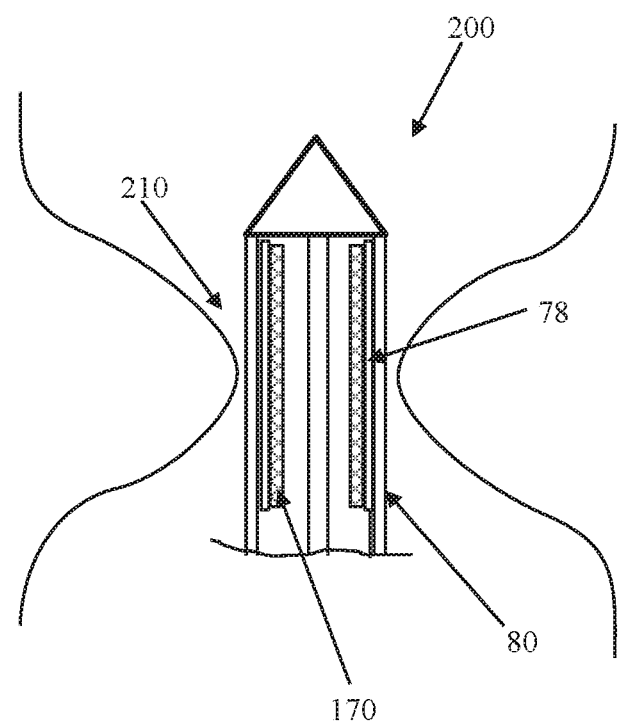
FIGS. 7A-7D illustrate use of the system of FIG. 6 in repairing a heart valve in accordance with methods of the present disclosure.
Figure 7B:
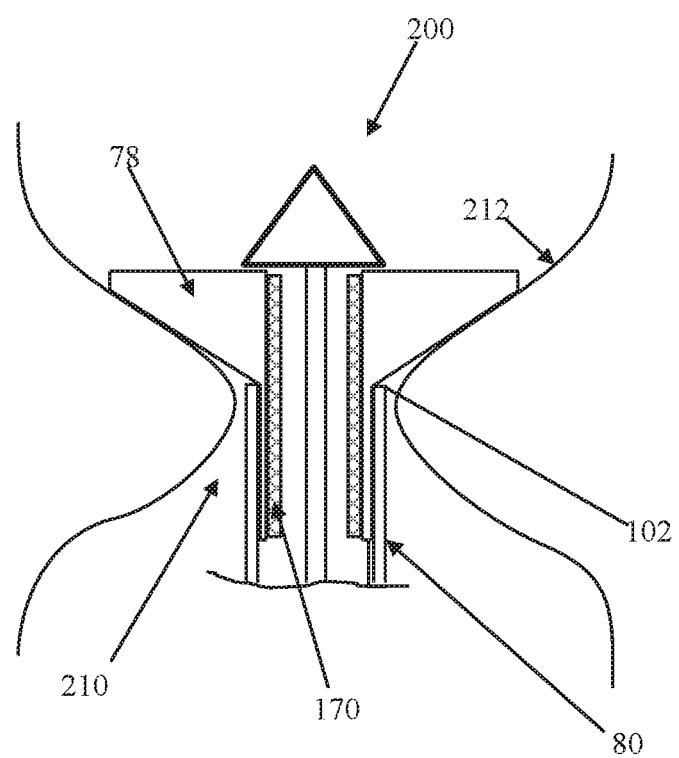

Use of the system 200 in providing a therapeutic treatment to a defective heart valve (e.g., repairing a defective heart valve) in accordance with methods of the present disclosure can be described with reference to FIGS. 7A-7D. The system 200, in the delivery state, is manipulated through a vasculature of the patient (e.g., via a percutaneous entry point in a femoral vein) to locate the prosthetic heart valve 170 at a target site 210 of the patient's heart (or other anatomical location) as in FIG. 7A. The target site 210 is depicted schematically in FIG. 7A and can be, for example, a mitral valve, aortic valve, tricuspid valve, or pulmonary valve. With the system 200 now located relative to the target site 210 as desired, the balloon 78 is incrementally pressurized (e.g., an inflation medium is forced into the inflation chamber 156 (FIG. 4B)) and the capsule 80 is incrementally retracted. In some embodiments, the clinician or other user can simultaneously control inflation of the balloon 78 and proximal retraction of the capsule 80 at the handle assembly 76 (FIG. 3). Regardless, with initial retraction of the capsule 80 and simultaneous inflation of the balloon 78, a region of the balloon 78 distal the distal end 102 of the capsule 80 radially expands as depicted in FIG. 7B. The capsule 80 as well as the supplied inflation pressure prevents the region of the balloon 78 proximal the distal end 102 from radially expanding. The exposed region of the balloon 78 expands into contact with anatomy 212 (referenced generally) of the target site 210 (e.g., walls of the patient's heart). Due to compliancy of the balloon 78, the contacted anatomy 212 experiences minimal trauma. However, the contacted anatomy 212 resists the radially outward or expansive force of the inflating balloon 78, transferring those forces radially inwardly on to the prosthetic heart valve 170. Thus, the inflating balloon 78 serves to maintain the prosthetic heart valve 170 in the compressed or collapsed condition. In other words, absent the inflating balloon 78, the region of the prosthetic heart valve 170 distal the distal end 102 of the capsule 80 would self-expand toward the normal or expanded condition; the expanded balloon 78 (in combination with the contacted anatomy) prevents the exposed region of the prosthetic heart valve 170 from overtly self-expanding.

Figure 7C:
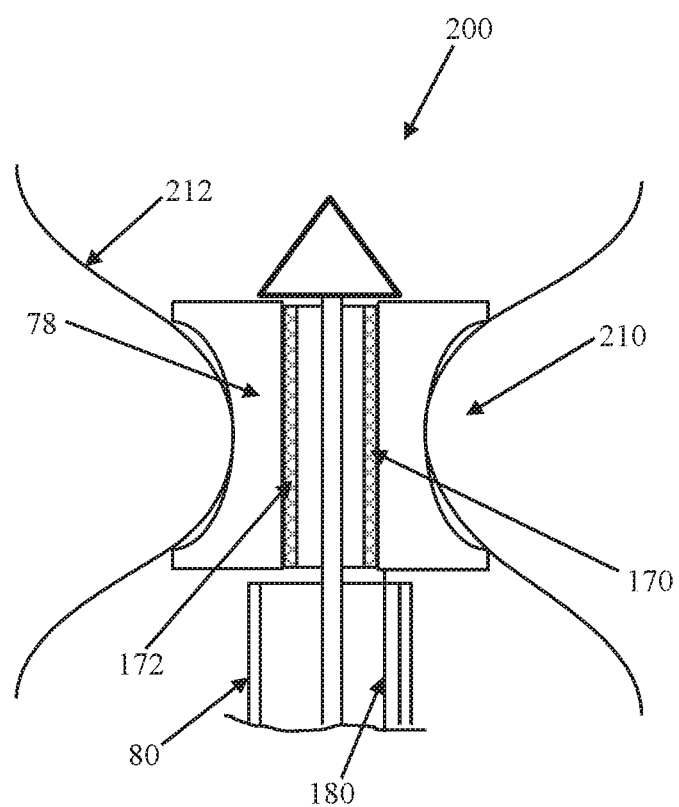

Incremental retraction of the capsule 80 and simultaneous, incremental increased pressure within the balloon 78 continues until the capsule 80 is fully retracted from over the balloon 78 and the prosthetic heart valve 170 as shown in FIG. 7C. In this intermediate deployment state, the balloon 78 remains connected to the supply line 180 and thus in an inflated arrangement. Further, the balloon 78 is in full contact with the anatomy 212 (e.g., wall(s) of the heart) of the target site 210, positioned between the anatomy 212 and the stent frame 172 of the prosthetic heart valve 170. With this arrangement, the pressurized balloon 78 maintains the prosthetic heart valve 170 in a collapsed condition. The balloon 78 is then gradually deflated (i.e., the inflation medium within the inflation chamber 156 (FIG. 4B) is gradually withdrawn via the supply line 180). As pressure within the balloon 78 is lessened, resistance to the expansion force generated by the stent frame 172 is removed, allowing the stent frame 172 to self-expand. A clinician or other user is thus afforded the ability to control the expansion and release of the stent frame 172 to desired rate(s).

Figure 7D:
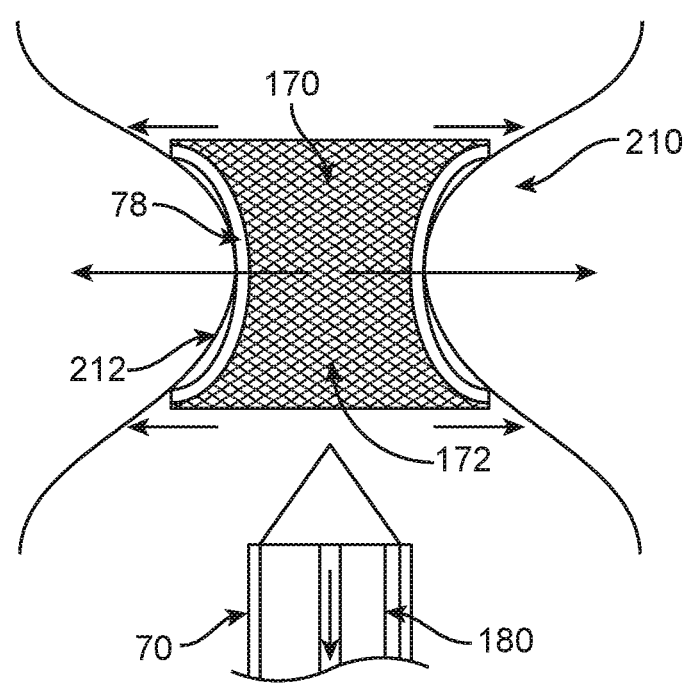

Once the balloon 78 is fully deflated, the prosthetic heart valve 170 is seated at the target site 210 due to the self-expanding construction of the stent frame 172 as in FIG. 7D. The balloon 78 is between the stent frame 172 and the anatomy 212 of the target site 210. In some embodiments, the supply line 180 is disconnected (e.g., severed) from the balloon 78, and a remainder of the delivery device 70 withdrawn from the patient. The balloon 78 thus remains in place, and is implanted with the prosthetic heart valve 170. The so-situated balloon 78 can beneficially provide a seal-like interface with the native anatomy 212, serving to minimize or prevent paravalvular leakage (PVL). In related embodiments in which a length of the balloon 78 is greater than a length of the stent frame 172, the balloon 78 can cover opposing ends or lips of the stent frame 172 to protect, encompass and further prevent PVL. In other embodiments, the balloon 78 can be retracted from the target site 210 with a remainder of the delivery device 70.

Figure 8:
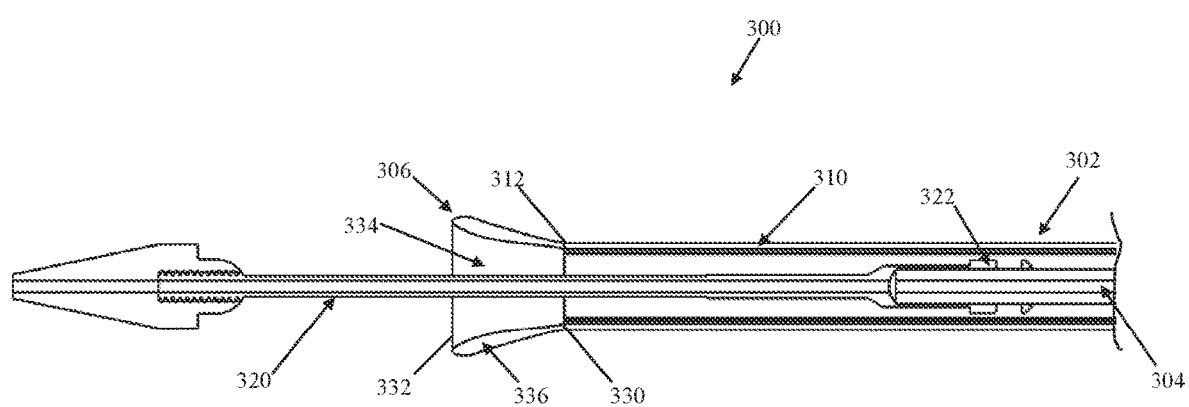
FIG. 8 is a cross-sectional view of a portion of another delivery device in accordance with principles of the present disclosure.

Portions of another embodiment delivery device 300 useful with systems and methods of the present disclosure are shown in FIG. 8. The delivery device 300 can be akin to the delivery device 70 (FIG. 3) described above, and generally includes a delivery sheath assembly 302, an inner shaft assembly 304, a handle assembly (not shown, but akin to the handle assembly 76 (FIG. 3) described above) and a balloon 306. As with previous embodiments, the delivery device 300 combines with a stented prosthetic heart valve (not shown) to form a system for performing a therapeutic procedure on a defective heart valve of a patient, such as repairing a defective heart valve. The delivery device 300 provides a loaded or delivery state in which a stented prosthetic heart valve is loaded over the inner shaft assembly 304 and is compressively retained within a capsule 310 of the delivery sheath assembly 302. As a point of reference, FIG. 8 depicts a deployment state of the delivery device 300 (and thus of the corresponding system) in which the balloon 306 projects distally beyond a distal end 312 of the capsule 310; in a delivery state, the balloon 306 is located within the capsule 310. In the illustrated embodiment, the balloon 306 is connected to the capsule 310 as described in greater detail below. In other embodiments, the balloon 306 can be separate from the capsule 310. Regardless, the balloon 306 is operable to control self-expansion or release of the prosthetic heart valve.

The inner shaft assembly 304 can be highly akin to the inner shaft assembly 74 (FIG. 3) described above, and can include a retention sub-assembly 320 providing a valve retainer 322. Similarly, the balloon 306 can be highly akin to the balloon 78 (FIG. 4B) described above, having a toroidal or hollow shape in extension between opposing, first and second ends 330, 332. As with previous embodiments, the balloon 306 defines a central passage 334 for receiving a prosthetic heart valve (not shown) and an inflation chamber 336.

Figure 9A:
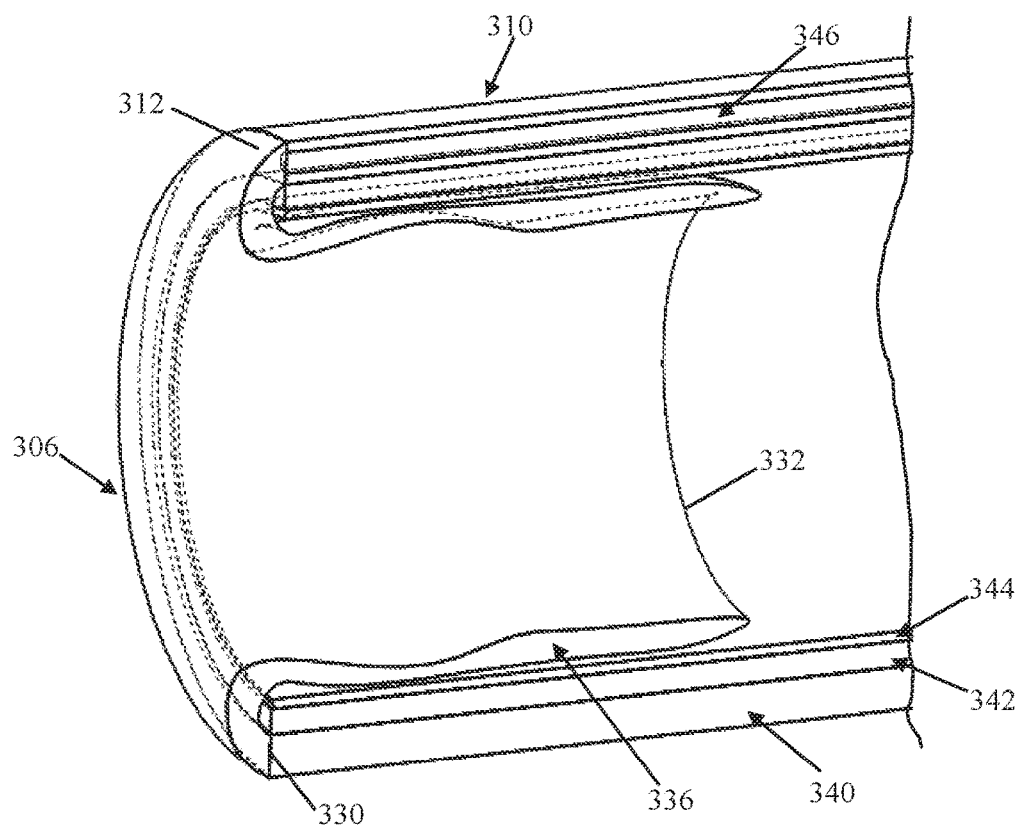
FIG. 9A is a perspective, cross-sectional view of a portion of the delivery device of FIG. 8, including a balloon and a capsule.
Figure 9B:
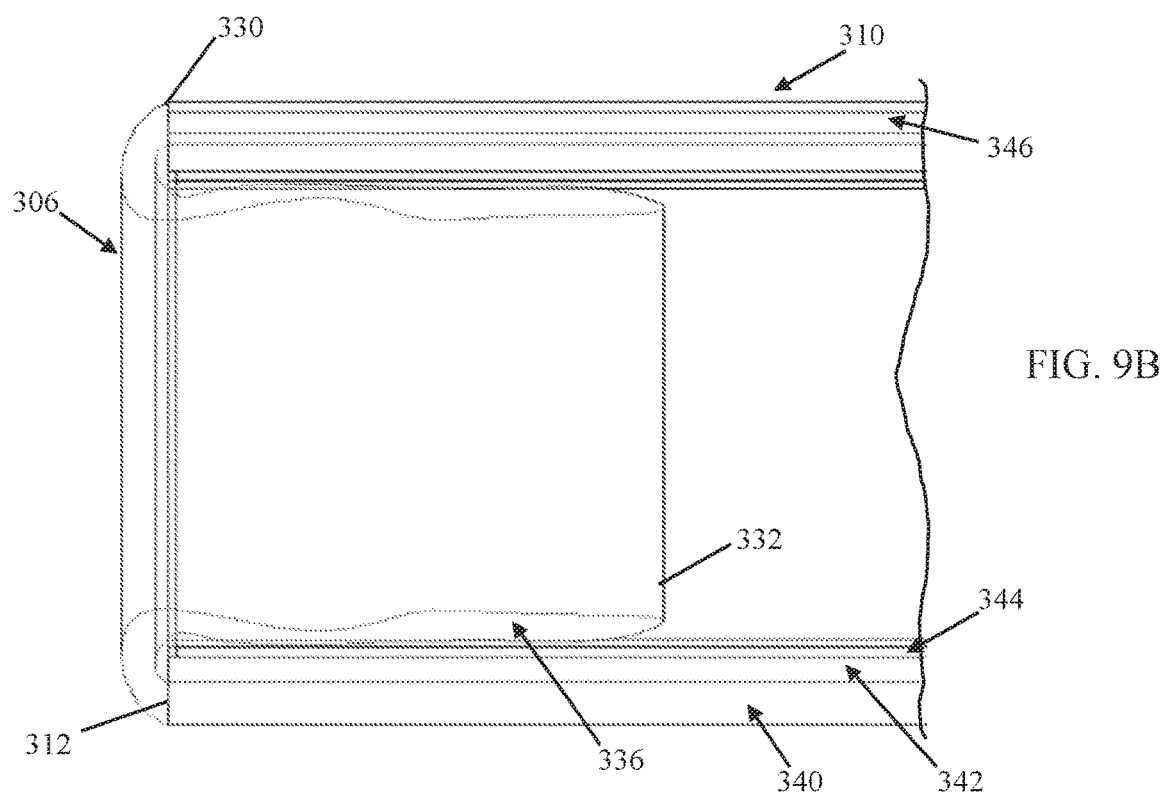
FIG. 9B is a longitudinal cross-sectional view of the portion of FIG. 9A.

The delivery sheath assembly 302 can be generally akin to the delivery sheath assembly 72 (FIG. 3) as described above, and includes the capsule 310 terminating at the distal end 312. In some embodiments, the delivery sheath assembly 302 is configured to directly support the balloon 306 and to provide a fluid connection or supply line to the inflation chamber 336. For example, the first end 330 of the balloon 306 can be connected or attached to the distal end 312 of the capsule 310. In the deployment state of FIG. 8, the balloon 306 is arranged to project distally beyond the distal end 312, with the second end 332 being distal the first end 330. In a delivery state, and as generally reflected by FIGS. 9A and 9B (that otherwise omits the inner shaft assembly 304), the balloon 306 is deflated and tucked or inverted into the capsule 310, with the second end 332 now being proximal the first end 330.

With the above designations in mind, the capsule 310 can incorporate a multi-layer design. For example, the capsule 310 can include an outer layer 340, an intermediate layer 342 and an inner layer 344. The outer layer 340 can be formed of a polymer or similar material, and defines an inflation lumen (or supply line) 346. For example, the outer layer 340 can be a surgically safe polymeric material molded to define the channel 346. A proximal end (not shown) of the inflation lumen 346 can be fluidly connected to source of pressure or inflation medium (not shown) as with previous embodiments. The intermediate layer 342 can be formed of a structurally robust material, selected to provide desired hoop strength characteristics (e.g., sufficient to maintain a stented prosthetic heart valve in a compressed condition). For example, the intermediate layer can be or include a metal, such as Nitinol™. In inner layer 344 can be formed of a polymer or similar material selected to facilitate a sliding interface with a prosthetic heart valve. Thus, the inner layer 344 can serve as an inner liner for the capsule. Other constructions having more or less of the layers 340-344 are also acceptable.

The first end 330 of the balloon 306 is attached (e.g., bonded) to the distal end 312 of the capsule 310, with the lumen 346 being fluidly open to the inflation chamber 336. With this construction, pressure or inflation medium delivered to the inflation chamber 336 via the lumen 346 causes the balloon 306 to "unfold" from the inverted arrangement of FIGS. 9A and 9B to the deployment arrangement of FIG. 8 in which the balloon 306 extends distally beyond the distal end 312 of the capsule 310. In other embodiments, the balloon 306 is not directly connected to the capsule 310; a supply line apart from the capsule 310 is provided to assist in inflating the balloon 306 at a location distally beyond the capsule 310. Regardless, when located outside of the capsule 310 and inflated, the balloon 306 radially expands.

Figure 10:
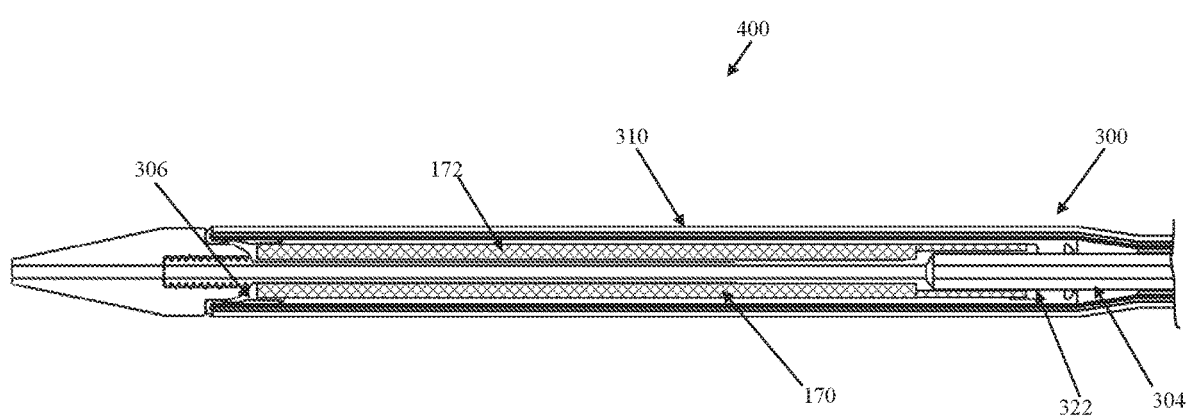
FIG. 10 is a longitudinal cross-sectional view of another system in accordance with principles of the present disclosure, including the delivery device of FIG. 6 and a prosthetic heart valve in simplified form.

In some embodiments, a length of the balloon 306 is less than a length of the prosthetic heart valve (not shown) to be deployed, optionally at least one-half the length of the prosthetic heart valve. For example, a portion of a system 400 in accordance with principles of the present disclosure, and including the delivery device 300 and the prosthetic heart valve 170 as described above, is provided in FIG. 10. In the delivery state of FIG. 10, the prosthetic heart valve 170 is loaded and maintained in a collapsed or crimped condition over the inner shaft assembly 304 by the capsule 310. The stent frame 172 is releasably connected to the valve retainer 322. The balloon 306 is in a deflated arrangement and is disposed over the prosthetic heart valve 170, radially between the stent frame 172 and the capsule 310. That is to say, the balloon 306 is inverted into the capsule 310, and is exteriorly located relative to the stent frame 172. As shown, a length of the balloon 306 is less than a length of the prosthetic heart valve 170; in some embodiments, the length of the balloon 306 is no greater than 25% of the length of the prosthetic heart valve 170. The capsule 310 is longitudinally moveable or slidable relative to the prosthetic heart valve 170 (and vice-versa). In the illustrated embodiment, the balloon 306 is attached to the capsule 310 and thus moves with movement of the capsule 310. In other embodiments, the balloon 306 can be apart from the capsule 310.

Use of the system 400 in providing a therapeutic treatment to a defective heart valve (e.g., repairing a defective heart valve) in accordance with methods of the present disclosure can be described with reference to FIGS. 11A-11E. The system 400, in the delivery state, is manipulated through a vasculature of the patient (e.g., via a percutaneous entry point in a femoral vein) to locate the prosthetic heart valve 170 at a target site 410 of the patient's heart (or other anatomical location) as in FIG. 11A. The target site 410 is depicted schematically in FIG. 11A and can be, for example, a mitral valve, aortic valve, tricuspid valve, or pulmonary valve. With the system 400 now located relative to the target site 410 as desired, the balloon 306 is incrementally pressurized (e.g., an inflation medium is forced into the inflation chamber 346 (FIG. 8)) and the capsule 310 is incrementally retracted. In some embodiments, the clinician or other user can simultaneously control inflation of the balloon 306 and proximal retraction of the capsule 310 at the handle assembly (not shown, but akin to the handle assembly 76 in FIG. 3).

Figure 11A:
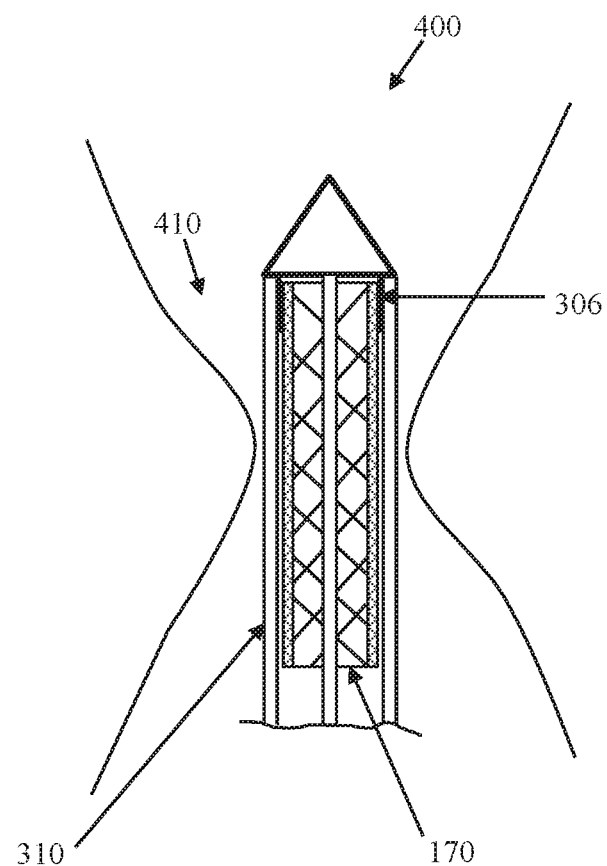
FIGS. 11A-11E illustrate use of the system of FIG. 10 in repairing a heart valve in accordance with methods of the present disclosure.
Figure 11B:
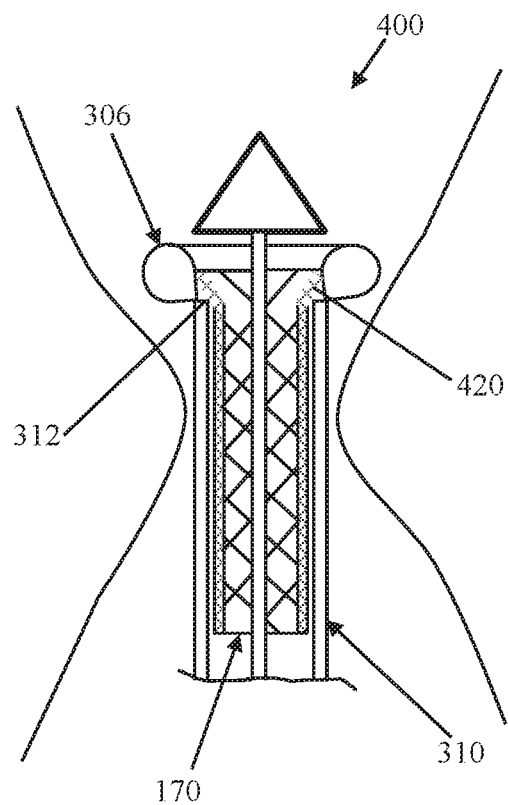

With initial retraction of the capsule 310 and simultaneous inflation of the balloon 306, the balloon 306 is caused to extend distally from the capsule 310 and radially expand or inflate as depicted in FIG. 11B. A section 420 of the prosthetic heart valve 170 is also exposed distal the distal end 312 of the capsule 310 and begins to self-expand. The balloon 306 is radially outside of and in contact with the exposed section 420, creating a funnel-like arrangement that slows or controls expansion of the exposed section 420. The balloon 306 thus creates a smoother transition from the collapsed or crimped condition to the expanded condition in the initial deployment state.

Figure 11C:
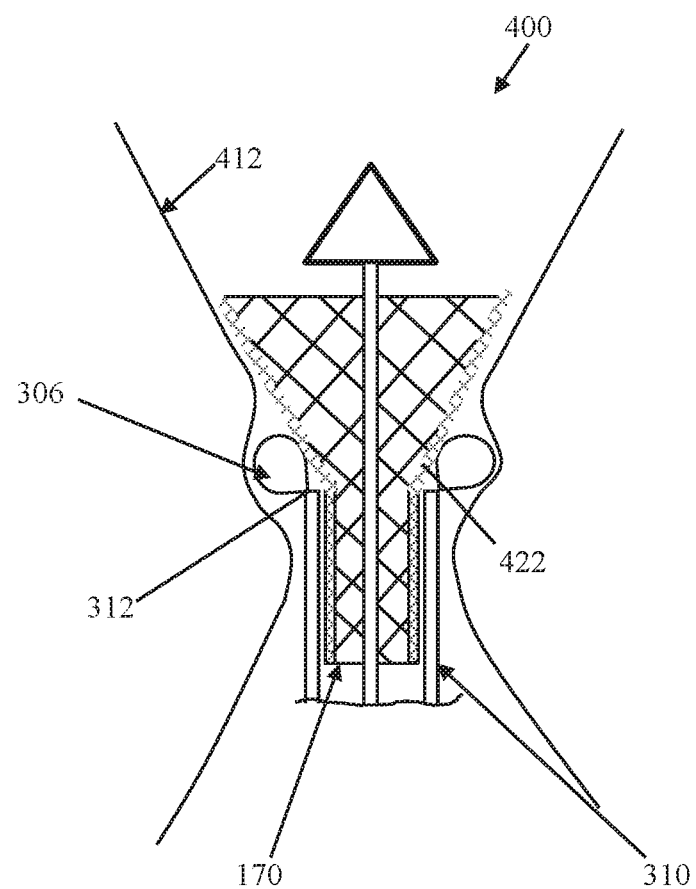

As the capsule 310 is further retracted, the balloon 306 is also retraced to retain the funnel effect at the deployment area of the prosthetic heart valve 170. For example, FIG. 11C illustrates a later stage of deployment. As compared to the stage of FIG. 11B, in FIG. 11C the capsule 310 and the balloon 306 have been further retracted relative to the prosthetic heart valve 170, such that an additional length of the prosthetic heart valve 170 is exposed and self-expands. The balloon 306 remains in contact with an exposed section 422 of the prosthetic heart valve 170 immediately distal the capsule distal end 312. Further, the balloon 306 (in the inflated arrangement) is in contact with anatomy 412 (referenced generally) of the target site 410 (e.g., walls of the patient's heart). Due to compliancy of the balloon 306, the contacted anatomy 412 experiences minimal trauma. However, the contacted anatomy 412 resists the radially outward or expansive force of the inflated balloon 306, transferring those forces radially inwardly on to the prosthetic heart valve 170. Thus, the balloon 306 serves to control expansion of the exposed section 422 akin to a funnel, serving as a pillow between the exposed section 422 and the contacted anatomy 412.

Figure 11D:
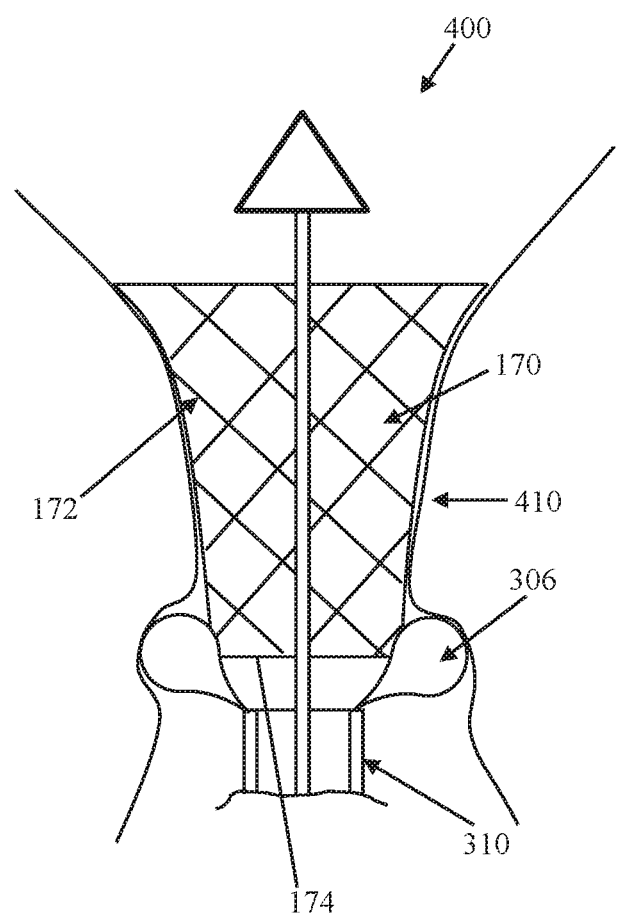
Figure 11E:
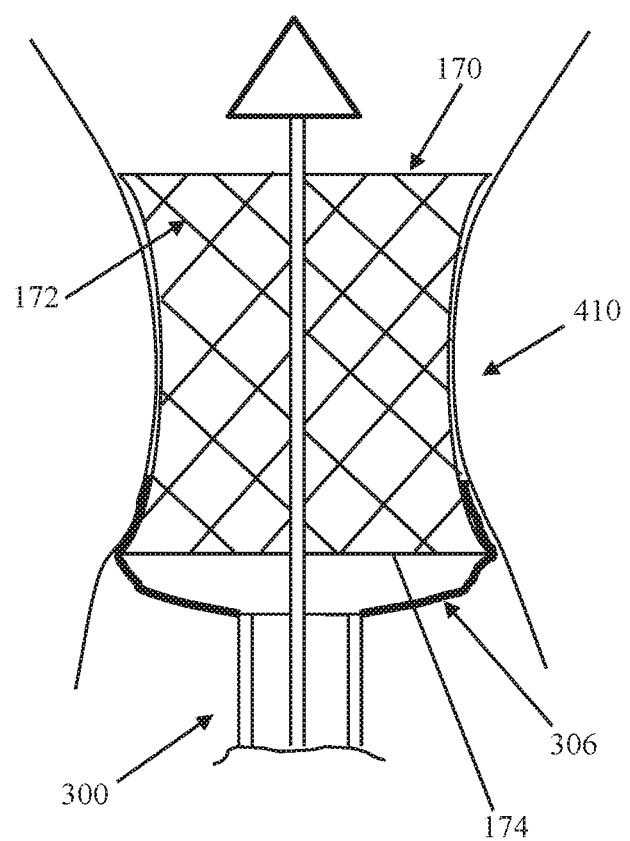

Retraction of the capsule 310 and the balloon 306 relative to the prosthetic heart valve 170 continues to the stage of FIG. 11D in which the balloon 306 is at an end 174 of the prosthetic heart valve 170. The balloon 306 is then deflated, as represented by FIG. 11E, allowing the end 174 to fully expand into engagement with the target site 410. In some embodiments, the stent frame 172 includes or provides retention members (not shown), such as paddles or arms, that can remain connected to the delivery device 300 while the balloon 306 is deflated. Regardless, following deflation of the balloon 306, the prosthetic heart valve 170 can be fully released from the delivery device 300. The delivery device 300, including the balloon 306, can then be removed from the patient.

The delivery devices, systems and methods of the present disclosure provide a marked improvement over previous designs. By providing an inflated balloon between a self-expanding prosthetic heart valve and the native anatomy, expansion of the prosthetic heart valve during deployment can be controlled.

Although the present disclosure has been described with reference to preferred embodiments, workers skilled in the art will recognize that changes can be made in form and detail without departing from the spirit and scope of the present disclosure. For example, while the devices and systems of the present disclosure have been described as being useful for delivering a stented prosthetic heart valve, a number of other implantable devices can be employed.

What is claimed is:

1. A system for repairing a defective heart valve of a patient, the system comprising: a delivery device including: an inner shaft assembly, a delivery sheath assembly slidably disposed over the inner shaft assembly, the delivery sheath assembly including a capsule terminating at a distal end; a balloon; and a prosthetic heart valve including a self-deploying stent carrying a prosthetic valve; wherein the system is configured to provide: a delivery state in which the capsule maintains the prosthetic heart valve in a collapsed condition over the inner shaft assembly, and the balloon is in a deflated arrangement radially between the prosthetic heart valve and the capsule, an initial deployment state in which at least a portion of the balloon and at least a portion of the prosthetic heart valve are located distal the distal end, with the at least a portion of the balloon in an inflated arrangement and surrounding an exterior of the at least a portion of the prosthetic heart valve, wherein the system is configured to further provide an intermediate deployment state in which: an entirety of the prosthetic heart valve is distally beyond the distal end of the capsule; and the at least a portion of the balloon is in the inflated arrangement between the exterior of the prosthetic heart valve and an anatomy of the patient, and further wherein the system is configured such that an entirety of the balloon is slidable relative to the prosthetic heart valve and the inner shaft assembly.

2. The system of claim 1, wherein the system is configured to further provide: a deployed state in which an entirety of the balloon and an entirety of the prosthetic heart valve are disconnected from the delivery device, including the balloon in the deflated arrangement and disposed between the exterior of the prosthetic heart valve and an anatomy of the patient.

3. The system of claim 1, wherein the system is configured to further provide: a final deployment state in which an entirety of the prosthetic heart valve and the at least a portion of the balloon are distal the distal end, and the balloon is in the deflated arrangement and disposed between the exterior of the prosthetic heart valve and an anatomy of the patient.

4. The system of claim 1, wherein the delivery device further includes an inflation lumen fluidly connected to an interior of the balloon in at least the delivery state.

5. The system of claim 4, wherein the inflation lumen is defined by a tubular body, and further wherein the delivery device further includes a severing mechanism for disconnecting the tubular body from the balloon.

6. The system of claim 4, wherein the inflation lumen is defined, at least in part, by the capsule.

7. The system of claim 1, wherein a longitudinal length of the balloon is greater than a longitudinal length of the prosthetic heart valve.

8. The system of claim 1, wherein a longitudinal length of the balloon is less than a longitudinal length of the prosthetic heart valve.

9. The system of claim 1, wherein the balloon has a toroid shape.

10. A system for repairing a defective heart valve of a patient, the system comprising:
a delivery device including:
an inner shaft assembly,
a delivery sheath assembly slidably disposed over the inner shaft assembly, the delivery sheath assembly including a capsule terminating at a distal end;
a balloon; and
a prosthetic heart valve including a self-deploying stent carrying a prosthetic valve;
wherein the system is configured to provide:
a delivery state in which the capsule maintains the prosthetic heart valve in a collapsed condition over the inner shaft assembly, and the balloon is in a deflated arrangement radially between the prosthetic heart valve and the capsule,
an initial deployment state in which at least a portion of the balloon and at least a portion of the prosthetic heart valve are located distal the distal end, with the at least a portion of the balloon in an inflated arrangement and surrounding an exterior of the at least a portion of the prosthetic heart valve;
wherein the delivery device further includes an inflation lumen fluidly connected to an interior of the balloon in at least the delivery state;
wherein the inflation lumen is defined by a tubular body, and further wherein the delivery device further includes a severing mechanism for severing the inflation lumen for disconnecting the balloon from the delivery device.

11. The system of claim 10, wherein the system is configured to further provide an intermediate deployment state in which:
an entirety of the prosthetic heart valve is distally beyond the distal end of the capsule; and
the at least a portion of the balloon is in the inflated arrangement between the exterior of the prosthetic heart valve and an anatomy of the patient.

12. The system of claim 11, wherein the system is configured to further provide:
a deployed state in which an entirety of the balloon and an entirety of the prosthetic heart valve are disconnected from the delivery device, including the balloon in the deflated arrangement and disposed between the exterior of the prosthetic heart valve and an anatomy of the patient.

13. The system of claim 11, wherein the system is configured to further provide:
a final deployment state in which an entirety of the prosthetic heart valve and the at least a portion of the balloon are distal the distal end, and the balloon is in the deflated arrangement and disposed between the exterior of the prosthetic heart valve and an anatomy of the patient.

14. The system of claim 10, wherein the inflation lumen is defined, at least in part, by the capsule.

15. The system of claim 10, wherein a longitudinal length of the balloon is greater than a longitudinal length of the prosthetic heart valve.

16. The system of claim 10, wherein a longitudinal length of the balloon is less than a longitudinal length of the prosthetic heart valve.

17. The system of claim 10, wherein the balloon has a toroid shape.

18. A system for repairing a defective heart valve of a patient, the system comprising:
- a delivery device including:
  - an inner shaft assembly,
  - a delivery sheath assembly slidably disposed over the inner shaft assembly, the delivery sheath assembly including a capsule terminating at a distal end;
- a balloon; and
- a prosthetic heart valve including a self-deploying stent carrying a prosthetic valve;
- wherein the system is configured to provide:
  - a delivery state in which the capsule maintains the prosthetic heart valve in a collapsed condition over the inner shaft assembly, and the balloon is in a deflated arrangement radially between the prosthetic heart valve and the capsule,
  - an initial deployment state in which at least a portion of the balloon and at least a portion of the prosthetic heart valve are located distal the distal end, with the at least a portion of the balloon in an inflated arrangement and surrounding an exterior of the at least a portion of the prosthetic heart valve;
- wherein the delivery device further includes an inflation lumen fluidly connected to an interior of the balloon in at least the delivery state;
- wherein the inflation lumen is defined by a tubular body, and further wherein the delivery device further includes a severing mechanism for disconnecting the tubular body from the balloon.

* * * * *